United States Patent
Zhu et al.

(10) Patent No.: US 9,581,629 B2
(45) Date of Patent: Feb. 28, 2017

(54) SENSOR SLEEVE FOR HEALTH MONITORING OF AN ARTICLE

(71) Applicants: Parker-Hannifin Corporation, Cleveland, OH (US); University of Cincinnati, Cincinnati, OH (US)

(72) Inventors: Xiangdong Zhu, Dublin, OH (US); Peter V. Buca, Sandusky, OH (US); Jay Lee, Mason, OH (US); Mark Schulz, West Chester, OH (US); Surya Sundaramurthy, Cincinnati, OH (US); Vesselin Shanov, Cincinnati, OH (US)

(73) Assignee: Parker Hannifin Corporation, Cleveland, OH (US)

( * ) Notice: Subject to any disclaimer, the term of this patent is extended or adjusted under 35 U.S.C. 154(b) by 0 days.

(21) Appl. No.: 14/794,444

(22) Filed: Jul. 8, 2015

(65) Prior Publication Data
US 2015/0309099 A1    Oct. 29, 2015

Related U.S. Application Data

(63) Continuation of application No. 13/697,435, filed as application No. PCT/US2011/036190 on May 12, 2011.
(Continued)

(51) Int. Cl.
*G01N 27/00* (2006.01)
*G01M 3/18* (2006.01)
(Continued)

(52) U.S. Cl.
CPC .......... *G01R 27/2605* (2013.01); *G01L 9/003* (2013.01); *G01M 3/18* (2013.01);
(Continued)

(58) Field of Classification Search
CPC .. G01R 27/2605; G01R 27/26; H05K 1/0298; H05K 1/115; H05K 41/053;
(Continued)

(56) References Cited

U.S. PATENT DOCUMENTS

| | | | |
|---|---|---|---|
| 4,029,889 A | * | 6/1977 | Mizuochi .............. G01M 3/165 138/103 |
| 5,267,670 A | | 12/1993 | Foster |

(Continued)

FOREIGN PATENT DOCUMENTS

| | | |
|---|---|---|
| DE | 31 40 804 | 4/1983 |
| GB | 2 373 057 A | 9/2002 |

(Continued)

OTHER PUBLICATIONS

European Search Report for corresponding EP application 13185354.1 dated Nov. 21, 2013.
(Continued)

*Primary Examiner* — Jermele M Hollington
*Assistant Examiner* — Taqi Nasir
(74) *Attorney, Agent, or Firm* — Renner, Otto, Boisselle & Sklar, LLP

(57) ABSTRACT

A sensor sleeve for use in detecting a failure in an article (e.g., a hydraulic hose), the sensor sleeve includes an insulator layer that separates two electrode layers. As such, the electrode layers deform to contact each other, which changes the impedance as measured across the electrode layers. The sensor sleeve is designed to change electrical impedance (resistance) due to fluid pressure initiating a hole through the sensor itself. The sensor sleeve will detect the fluid leak when the hole penetrates the sensor and brings the two elastic electrodes in contact with each other and/or the fluid, which when the fluid is conductive fluid, creates a signal path between the first electrode layer and the second
(Continued)

electrode layer, which also changes the impedance as measured across the electrode layers.

20 Claims, 14 Drawing Sheets

Related U.S. Application Data

(60) Provisional application No. 61/333,828, filed on May 12, 2010.

(51) Int. Cl.
*G01R 27/26* (2006.01)
*G01N 27/20* (2006.01)
*G01N 27/24* (2006.01)
*G01L 9/00* (2006.01)

(52) U.S. Cl.
CPC ............ *G01M 3/182* (2013.01); *G01N 27/20* (2013.01); *G01N 27/24* (2013.01)

(58) Field of Classification Search
CPC .... H05K 2924/002; G01D 5/24; G01D 5/241; G01D 5/2417; G06K 9/0002
USPC ....... 324/658, 347, 449, 515, 220, 452, 453, 324/548, 519, 661–663, 671, 686, 76.11, 324/750.17; 73/49.5, 146, 1.57, 37, 700, 73/760, 795
See application file for complete search history.

(56) References Cited

U.S. PATENT DOCUMENTS

| 5,343,738 A | * | 9/1994 | Skaggs ................. F16L 11/121 138/113 |
| 5,551,484 A | | 9/1996 | Charboneau |
| 2004/0065377 A1 | | 4/2004 | Whiteley |
| 2006/0192465 A1 | * | 8/2006 | Kornbluh .................. B64C 3/48 310/309 |
| 2006/0196252 A1 | | 9/2006 | Deckard |
| 2007/0131035 A1 | | 6/2007 | Krutz et al. |
| 2009/0220190 A1 | | 9/2009 | Zandiyeh et al. |
| 2010/0007325 A1 | * | 1/2010 | Stark ..................... F16L 11/127 324/71.1 |
| 2012/0136592 A1 | | 5/2012 | Pereira et al. |

FOREIGN PATENT DOCUMENTS

| GB | 2373057 A | * | 9/2002 |
| GB | 2 435 519 | | 8/2007 |
| GB | 2 436 519 | | 10/2007 |
| WO | 2008/001238 | | 1/2008 |

OTHER PUBLICATIONS

International Search Report for International Application No. PCT/US2011/036190 dated Jul. 28, 2011.
European Examination Report dated Feb. 22, 2016 for corresponding European Application No. 13185354.1 dated May 12, 2011.

* cited by examiner

SENSOR SLEEVE FOR HEALTH MONITORING OF AN ARTICLE

RELATED APPLICATION DATA

The present application is a Continuation of U.S. application Ser. No. 13/697,435 filed Feb. 6, 2013, which is a national stage entry of International Application No. PCT/US11/36190 filed on May 12, 2011, which claims the benefit of the filing date of U.S. Provisional Patent Application Ser. No. 61/333,828 filed May 12, 2010, each of which is incorporated herein by reference in its entirety.

TECHNICAL FIELD

The present invention relates to a sensor sleeve for detecting damage to a pressurized article (e.g., a hydraulic hose).

BACKGROUND

A hydraulic connector hose is a tube that transfers fluids under pressure from one place to another. A hydraulic hose is a composite structure primarily made of rubber or thermoplastic and steel reinforcement. The steel reinforcement may include wire that is tightly wound spirally along the length of the hose so as to form a steel shell or it might be braided across the length of the hose for higher strength. The outermost covering is usually made of polymer material that helps protect the inner layers from harsh environments. Hydraulic hoses operate from a very low pressure to extremely high pressure depending on the applications. Hydraulic hoses are used in a variety of industries like heavy-machinery, household appliances etc and environments. In certain situations, especially in heavy machinery, the health of a hose is critical.

A hydraulic hose has a finite service life and all hoses eventually fail due to various factors like external damage, multi-plane bending, operating conditions, etc. The damage to a hose carrying such high pressures can lead to serious injury or death of an operator. Hence, monitoring the health of the hose becomes critical.

Conventional technology depicted by U.S. Pat. No. 7,555,936 to Purdue Research Foundation and PCT Publication No. WO 2010/004418 to Eaton Corporation generally uses the hydraulic hose as a sensor. For example, the above listed references use the principle of capacitance measurement wherein the capacitance of the hose is measured and used as the health indicator of the hose. Problems with such methods include: hose metal layers may come in contact with each other due to crimping, for example; does not consider a hose with other than two metal layers; and discounts the damage to the hose caused from a foreign object.

SUMMARY

The present invention is directed to a variety of sensor sleeves for use in detecting a failure in an article (e.g., a hydraulic hose). The sensor sleeves generally include an insulator layer that separates two electrode layers. As such, the electrode layers deform to contact each other. In general, but not all cases, the electrode layers are thicker and flexible relative to the insulator (dielectric) layer.

The sensor sleeve is designed to change electrical impedance due to fluid pressure or a foreign object pushing against or through the sensor itself. The sensor sleeve will detect an oil leak or foreign object through the hose when a hole is formed by fluid pressure or foreign object, which deforms and/or penetrates the sensor and brings the two elastic electrodes in contact with each other. The flexibility, thickness and geometry of the electrodes may be designed based on the material the sensor skin is monitoring. As an example, to monitor a composite material for impact damage, the sensor skin would have thinner and stiffer electrodes to match the impedance (stiffness) of the base composite material. The phrase "composite material" is used herein to describe elastomeric composite materials (e.g., hoses) and also fiber reinforced polymer composite materials (e.g., a composite airplane wing). A composite hose is a combination of rubber material and steel wire. A fiber reinforced polymer composite is a combination of strong fibers embedded in a polymer matrix (e.g., carbon fibers embedded in epoxy or prepreg carbon fabric layered to form a panel). Other types of composites are also possible. The sensor sleeve may include electrodes and a dielectric specifically designed for the different types of composite materials that can be monitored.

Another aspect of the invention relates to a sensor sleeve designed to change capacitance due to the deformation of itself caused by fluid leakage or damage caused by a foreign object. In such, embodiment, the dielectric layer may be thicker then the electrode layers. Such a sensor should be carefully designed so it only accounts for critical damages from fluid leakage or foreign object impact.

Another aspect of the invention relates to a sensor sleeve for detecting damage to a surface of an article, the sensor sleeve including: a first electrode layer covering at least a portion of a surface of an article; a dielectric layer covering a least a portion of the first electrode layer; and a second electrode layer covering at least a portion of the dielectric layer, wherein damage to the surface of the article covered by the first electrode layer, the dielectric layer and the second dielectric layer causes the first electrode layer to contact the second electrode layer, thereby decreasing the impedance between the first electrode layer and the second electrode layer.

Another aspect of the invention relates to a method for detecting failure of an article, the method including: monitoring impedance of an article, wherein the article includes a sensor sleeve including a first electrode layer covering at least a portion of a surface of the article; a dielectric layer covering a least a portion of the first electrode layer; and a second electrode layer covering at least a portion of the dielectric layer, wherein damage to the surface of the article covered by the first electrode layer, the dielectric layer and the second electrode layer causes the first electrode layer to contact the second electrode layer, wherein the impedance is measured between the first electrode layer and the second electrode layer; and detecting a failure in the article based at least in part on the monitored impedance across the first electrode layer and the second electrode layer.

Another aspect of the present invention relates to a method of manufacturing a sensor sleeve over an article, the method including: applying a first electrode layer over at least a portion of an article; applying a dielectric layer over at least a portion of the first electrode layer; and applying a second electrode layer at least a portion of the dielectric layer.

Another aspect of the present invention relates to a sensor sleeve for detecting conductive fluid leakage in an article, the sensor sleeve including: a first electrode layer covering at least a portion of a surface of the article; a dielectric layer covering a least a portion of the first electrode layer, wherein the dielectric layer is a porous and non-absorbent dielectric layer; and a second electrode layer covering at least a portion of the dielectric layer, wherein fluid leakage from the article creates a conductive path through the dielectric layer and between the first electrode layer and the second electrode layer.

Another aspect of the present invention relates to a method for detecting conductive fluid leaking in an article, the method including: monitoring impedance of an article, wherein the article includes a sensor sleeve including a first electrode layer covering at least a portion of a surface of the article; a dielectric layer covering a least a portion of the first electrode layer, wherein the dielectric layer is porous and non-conductive; and a second electrode layer covering at least a portion of the dielectric layer, wherein a leak of conductive fluid creates a conductive path through the dielectric layer and between the first electrode layer and the second electrode layer, wherein the impedance is measured between the first electrode layer and the second electrode layer; and detecting the leak of conductive fluid in the article based at least in part on the monitored impedance across the first electrode layer and the second electrode layer.

Another aspect of the invention relates to the sensor sleeve being designed to change capacitance due to the deformation of the sensor, which may be caused by fluid pressure (e.g., an oil leak) or damage caused by a foreign object. In such cases, the dielectric layer may be thicker than the two electrode layers, for example. Such sensor needs to be carefully designed so it may account for critical damages caused from fluid pressure and foreign object impact, for example.

Another aspect of the present invention relates to placement of the sensor sleeve. The sensor sleeve may be placed or formed on the outside of the hose, or anywhere inside the article between the hose layers. When the sensor sleeve, is formed inside the hose, one or more hose layers can function as one or more of the sensor sleeve layers.

Other systems, devices, methods, features, and advantages of the present invention will be or become apparent to one having ordinary skill in the art upon examination of the following drawings and detailed description. It is intended that all such additional systems, methods, features, and advantages be included within this description, be within the scope of the present invention, and be protected by the accompanying claims.

It should be emphasized that the term "comprise/comprising" when used in this specification is taken to specify the presence of stated features, integers, steps or components but does not preclude the presence or addition of one or more other features, integers, steps, components or groups thereof."

BRIEF DESCRIPTION OF THE DRAWINGS

Embodiments of this invention will now be described in further detail with reference to the accompanying drawings, in which.

DETAILED DESCRIPTION OF EMBODIMENTS

Aspects of the present invention are directed to a variety of sensor sleeves. As used herein, the term "sleeve" includes a skin, a sheath, an outer cover and a structure formed within a hose component, for example.

Figure 1:
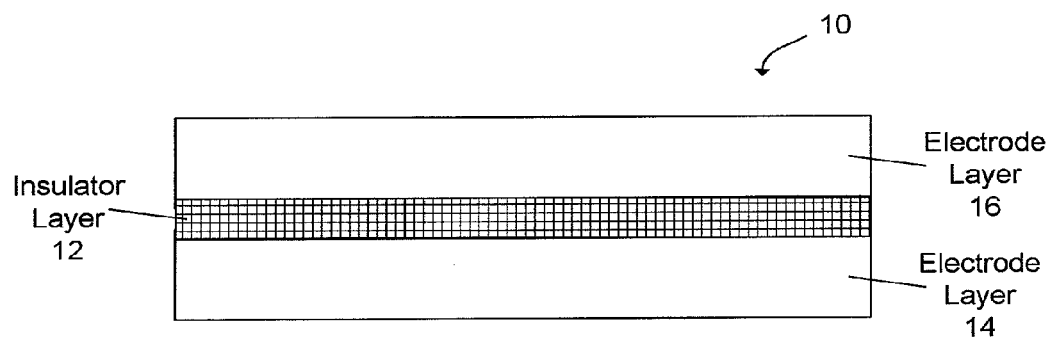
FIG. 1 is an exemplary sensor sleeve in accordance with aspects of the present invention.

Referring to FIG. 1, a cross-section of an exemplary sensor sleeve 10 in accordance with aspects of the present invention is illustrated. The sensor sleeve 10 generally includes an insulator layer 12 that separates to a first electrode layer 14 and a second electrode layer 16. As described below, in general, the electrode layers 14, 16 deform to contact each other when a fault or failure condition occurs. Thus, the electrode layers 14, 16 are usually thicker and flexible relative to the insulator (dielectric) layer 12.

Figure 2:
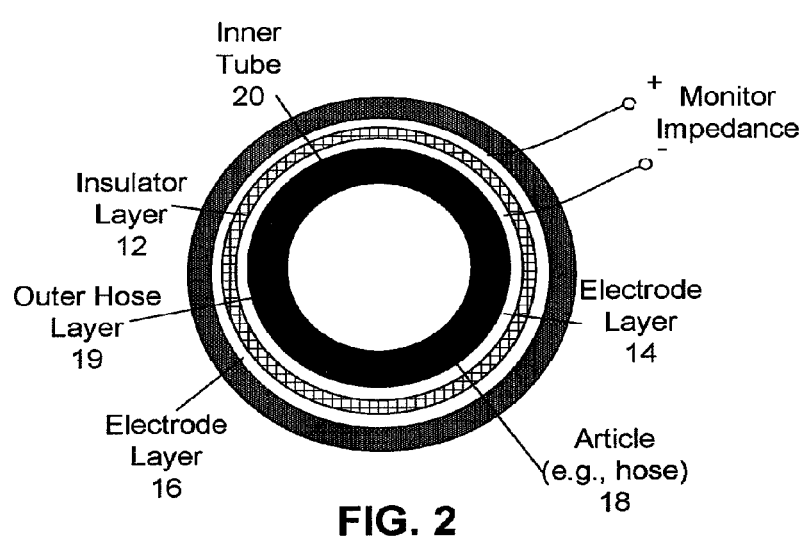
FIG. 2 is a cross-section of the sensor sleeve of FIG. 1 covering an article in accordance with aspects of the present invention.

Referring to FIG. 2, the sensor sleeve 10 is illustrated covering the surface of an article 18. For example, the article may be a hose. The article 18 is representative of various types of hoses that may be used to contain a flowing or static fluid. A particular example is a hydraulic hose that contains a hydraulic fluid whose pressure fluctuates. As such, the article 18 may have a circumferential surface and is operable to transfer fluids from one place to another. The article 18 has an inner tube 20 that contacts a fluid flowing through the article 18. The article 18 may include one or more reinforcement layers (not shown) that strengthen the article 18, and an outer cover 19 that protects the article 18 and its interior components. Because the inner tube 20 directly contacts the fluid, the material from which the inner tube 20 is formed must be chemically compatible with the fluid contained by the article 18. As a result, various materials may be employed for the inner tube 20, including nitrile-butadiene, chloroprene, copolymer of ethylene and propylene, polytetrafluoroethylene (PTFE), etc. The reinforcement layer generally promotes the strength of the article 18. Any number of reinforcement layers may be present in the article 18, and reinforcement layers may be constructed from a variety of materials in a variety of configurations. Typical materials include metals such as steels, bronze, and aluminum, synthetic materials such as rayon, nylon, polyethylene terephthalate (PET) fiber, and glass fiber, and textile yarns such as cotton. If multiple reinforcement layers are used, rubber separation layers may be placed between the reinforcement layer to reduce abrasion and wear there between.

Suitable materials for the outer cover 19 will depend on the operating environment of the article 18 with typical materials including synthetic rubbers.

As illustrated in FIG. 2, the sensor sleeve 10 includes a first electrode layer 14 covering at least a portion of a surface of an article 18. An insulator (dielectric) layer 12 covers a least a portion of the first electrode layer 14. A second electrode layer 16 is illustrated covering at least a portion of the dielectric layer 12. When damage to the surface of the article 18 occurs, the first electrode layer 14 is caused by fluid pressure exerted through the inner tube 20 and the sidewalls of the article 18 to contact the second electrode layer 16. When the electrode layers 14, 16 make contact, the impedance measured between the electrode layers decreases from the mega-Ohms range when the electrode layers 14, 16 are not in contact (and isolated) to near zero when the electrode layers 14, 16 are in contact with each other.

The sensor sleeve 10 is also responsive to damage caused by external sources (e.g., force impact). When damage to the electrode layer 16 occurs, the electrode layer 16 is caused by the external force to penetrate the insulator layer 12 and contact the first electrode layer 14. When the electrode layers 14, 16 make contact, the impedance measured between the electrode layers decreases from the mega-Ohms range when the electrode layers 14, 16 are not in contact (and isolated) to near zero when the electrode layers 14, 16 are in contact with each other.

In order to facilitate contact between the electrode layers 14, 16, one or more of the electrode layers may include contacts 22 (also referred to herein as protrusions, penetrators, etc.) embedded in and/or formed from the electrode layer 14, 16. For example, referring to FIGS. 3 and 4, the electrode layer 14 may include one or more contacts 22 spaced apart, wherein the contacts are configured to puncture through the dielectric layer 12 and make contact with the second electrode layer 16 when a crack and/or leak develops in the article 18.

Figure 3:
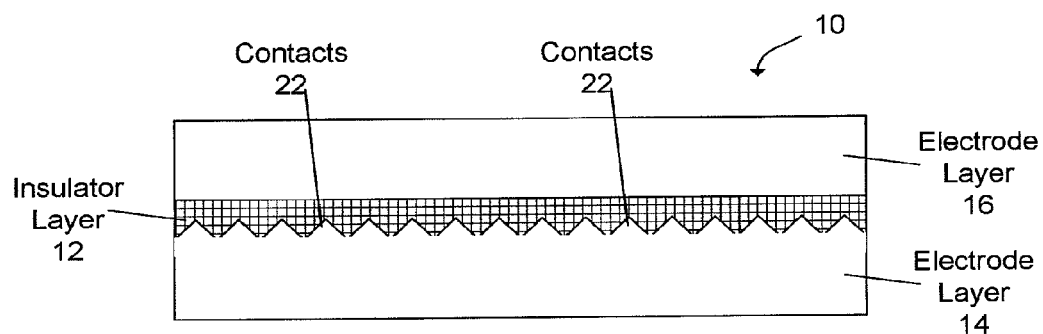
FIGS. 3-9 are exemplary sensor mechanisms in accordance with aspects of the present invention.
Figure 4:
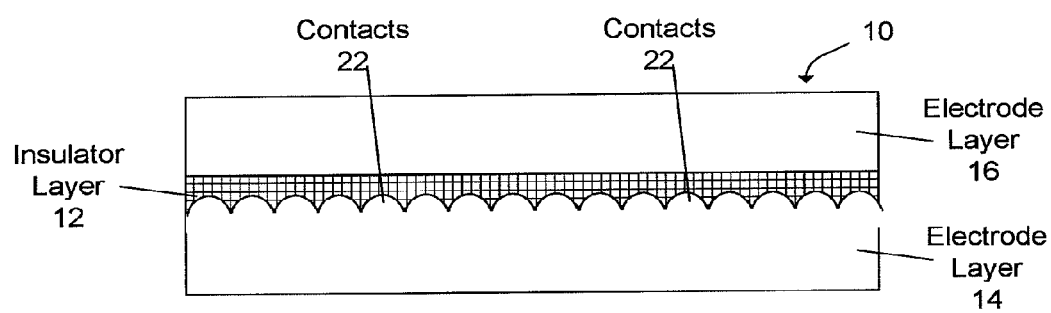
Figure 5:
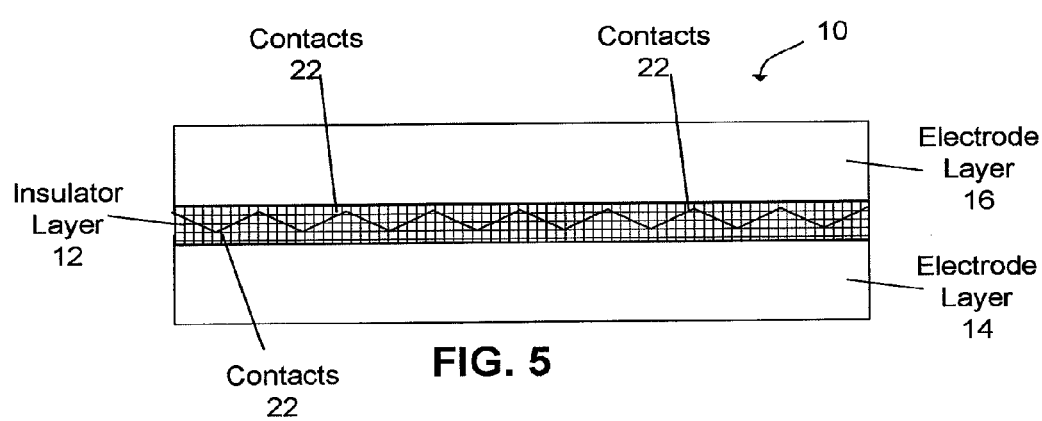

Any shape of contact 22 may be used in accordance with aspects of the present invention. For example, as shown in FIG. 3, the contacts 22 have a saw-tooth shape. With respect to FIG. 4, the contacts 22 have a semi-circle shape. One of ordinary skill in the art will readily appreciate that the contacts 22 may be any desired size and shape and may be dependent on application. Likewise, the contacts 22 may be spaced apart a prescribed uniform distance and/or a non-uniform distance. The contacts 22 facilitate contact between the electrode layers 14, 16 upon initiation of a damage condition associate with the article 18. In another embodiment, illustrated in FIG. 5, the contacts 22 may take the form of a wire embedded in the dielectric layer 12, for example.

The sensor sleeve 10 may be designed to change electrical impedance (or resistance) due to a fluid pressure (e.g., oil pressure) initiating a pin hole through the sensor sleeve 10. The sensor sleeve 10 will detect the fluid leak when the pin hole penetrates the sensor sleeve 10 and brings the two elastic electrode layer 14, 16 in contact with each other. The flexibility, thickness and geometry of the electrode layers 14, 16 should be designed based on the material the sensor sleeve is monitoring, e.g. an article in the form of a hydraulic hose. As an example, to monitor a composite material for impact damage, the sensor skin may have thinner and stiffer electrode layers to match the mechanical impedance (stiffness) of the base composite material (e.g., the components that form the hose, composite airplane wing, etc.).

As set forth above, the sensor sleeve 10 utilizes an electrical impedance approach to detect small initiating damage over large surfaces. As stated above, the sensor skin includes two electrode layers 14, 16 separated by an insulator layer 12 (e.g., a dielectric material), thereby forming a capacitor. The sensor sleeve 10 is thin (e.g., 10-1000 microns thick) and can be attached, sprayed, extruded and/or co-extruded onto the surface of an article 18. Exemplary articles in accordance with aspect of the present invention include: a hose assembly, tire assembly, belt assembly, etc. Electrical impedance measurements are used to detect damage to the sensor sleeve 10 due to impact or high pressure, or cracking of the article underneath the sleeve. Such damage will puncture the dielectric layer 12, which results in the electrode layers 14, 16 contacting each other. This contact will cause the electrical impedance of the sensor sleeve 10 to change from initially a high impedance range (e.g., Mega-Ohms, Kilo-Ohms, etc.) to near zero, for example. Thus, initiating damage can be identified early and the component can be repaired or taken out of service before it fails.

Advantages of the sensor sleeve 10 include that it can detect a small amount of damage over very large areas that may have complex structural shapes and features, and only one or a small number of channels of data acquisition are needed to monitor the impedance. The sensor sleeve 10 can be very low cost and tailored to each application. No damage from external loading can occur to the structure without first being detected by the change in impedance of the sensor sleeve 10 or by damage to the sensor sleeve 10.

The type of material for the dielectric layer may include, for example, silicone rubber, epoxy, nanotube elastomer, plastic, honeycomb, polymer nanocomposite, etc. Such materials will allow use of the sensor sleeve 10 for different structural and component applications including flexible components like hoses, tires and belts, rigid structures like concrete, and stiff composite components and structures like aircraft and spacecraft.

The type of material for the electrode layer may include, for example, aluminum, steel, titanium, or any other suitable conductive material. Many variations of the electrode material, thickness, size of protrusions (e.g. contacts, penetrators, etc.), and the dielectric material and thickness are possible. A general guideline is that the mechanical impedance of the sensor sleeve 10 should match the mechanical impedance of the article in which it is used with. For example, when monitoring composite materials, a stiffer and thinner sensor sleeve is appropriate because the displacements and strains may be small and the loads may be large such as due to impact. For elastomer material, the sensor sleeve should be softer and thicker because the displacements and strains are larger and the loads are lower.

Figure 6:
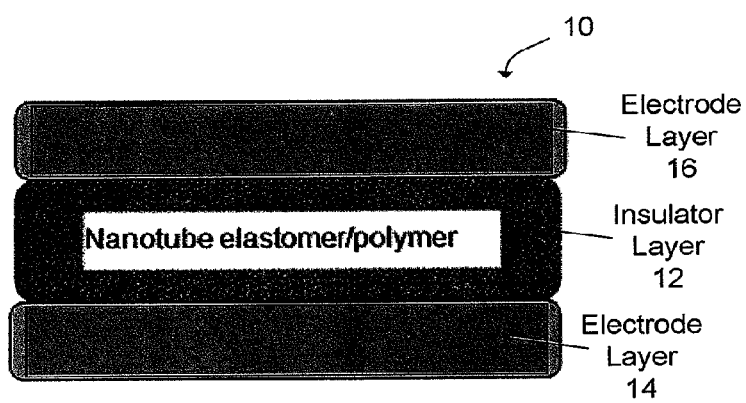

Different electrode configurations are possible for use with the sensor sleeve. FIG. 6 illustrates an embodiment wherein the sensor sleeve 10 includes a deformable (e.g. ductile like aluminum) metals in which the thickness of the electrode can vary so that damage would cause the outer electrode to deform into, and remain attached to the inner electrode thus shorting the sensor. Carbon nanotube arrays on one electrode surface, carbon nanotubes dispersed in the dielectric or insulator material, and different shape electrode surfaces could be built using nanotube synthesis on different substrates, dispersion of nanotubes in polymer and elastomers, and magnetron sputtering or other thin film deposition systems can be used to put patterns on the electrodes.

A few exemplary designs of a sensor sleeve 10 in accordance with aspects of the present invention are illustrated in FIGS. 6-9. With respect to FIG. 6, a piezoresistive elastomer or polymer that changes resistance with pressure and strain is illustrated in the insulator layer 12. A nanotube elastomer may be one example of such material. For example, nanotubes are dispersed in the insulator layer (e.g., within the elastomer/polymer) to provide the piezoresistivity. If the nanotube loading is at the percolation level, a large scale change in electrical impedance (or resistance) will occur with strain. This allows the sensor skin to be used as a pressure or strain sensor, as opposed to a binary (e.g., fault condition or no-fault condition) damage sensor.

Figure 7:
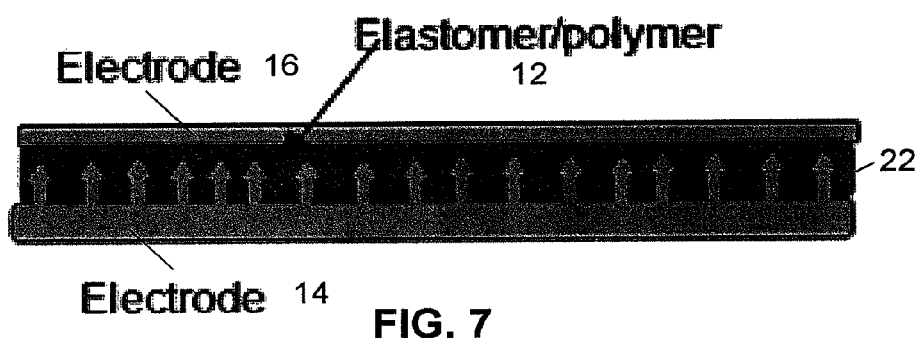

FIG. 7 illustrates spike contacts 22 formed in one electrode layer (e.g., electrode layer 14). When a failure condition arises, the contacts stay attached to the opposing electrode layer (e.g., electrode layer 16).

Figure 8A:
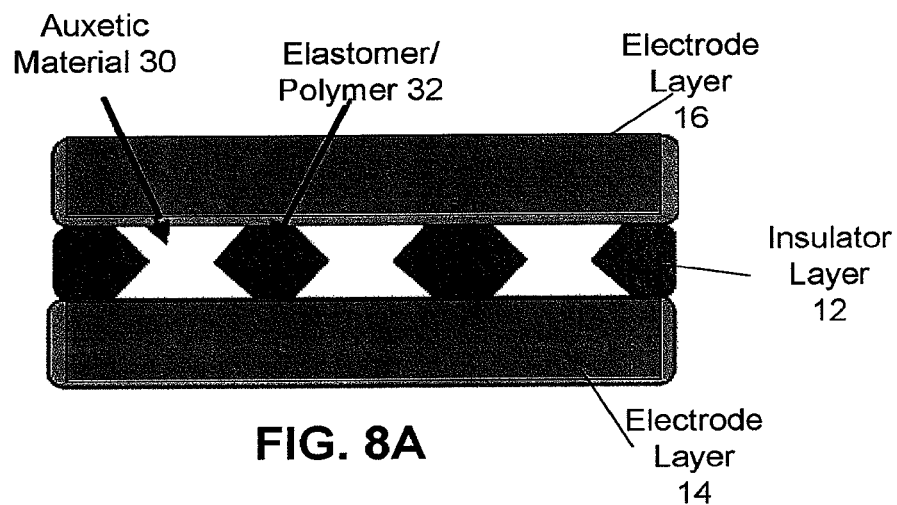
Figure 8B:
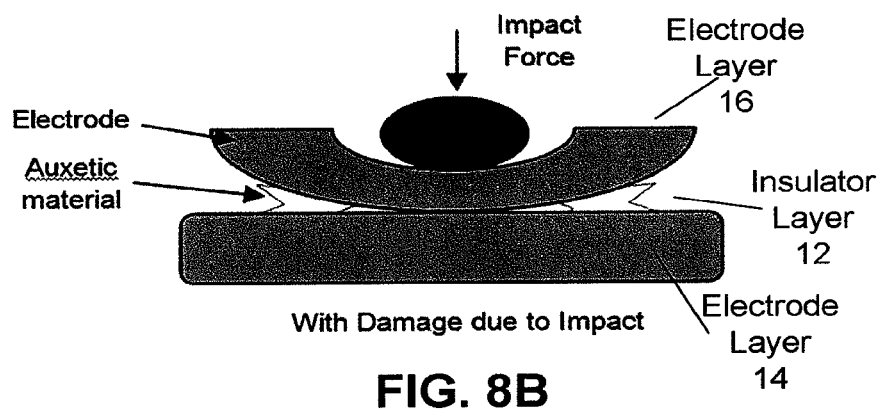

FIGS. 8A-8B illustrate use of an auxetic material 30, similar to a honeycomb material, that has a negative Poisson's ratio and an elastomer 32 positioned between the auxetic material to achieve a desired stiffness of the insulator layer 12. In one embodiment, the auxetic material may be used to provide a non-linear stiffness dielectric layer. In another embodiment, the auxetic material 30 may be used to facilitate collapsing of the sensor if used as an insulating layer. FIG. 8B illustrates the auxetic material collapsing due to an external impact force imparted on one portion of the sensor sleeve 10. The external impact force imparts sufficient force to collapse the auxetic material and enables the electrode layers 14, 16 to make contact with each other, which changes the impedance measured between the electrode layers 14, 16.

Figure 9:
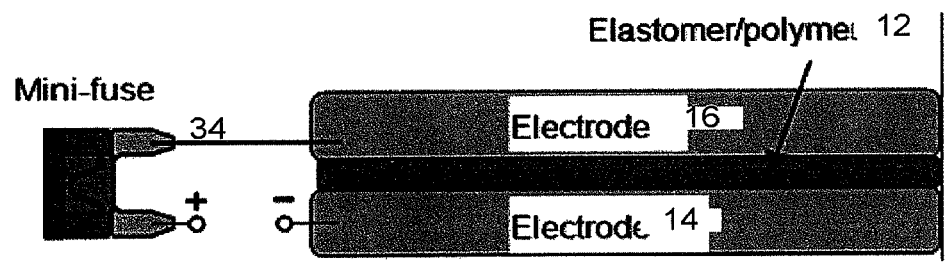

FIG. 9, illustrates a fuse 34 or alarm in series with a battery (not shown). Once the electrodes contact each other, the fuse is blown, which interrupts some process or stops the hydraulic system, or an alarm can sound in place of or with the fuse. Further implementation of system that uses aspects of this embodiment will be discussed below.

Figure 10A:
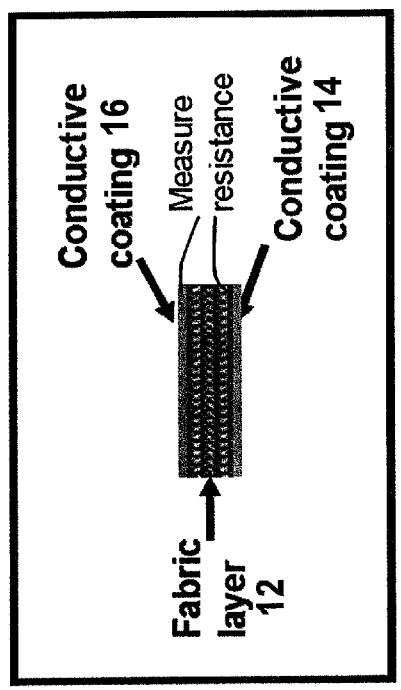
FIGS. 10A-10B are sensor sleeves for detecting fluid leak in an article in accordance with aspects of the present invention.
Figure 10B:
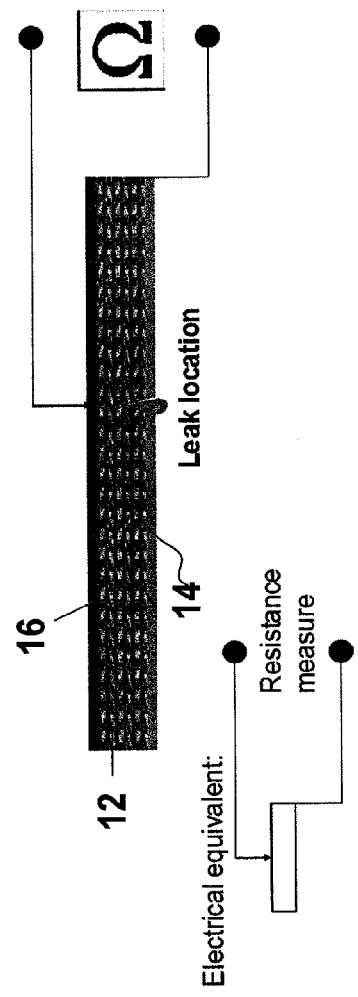

Another embodiment of the invention is illustrated in FIGS. 10A and 10B. In FIG. 10, the sensor sleeve 10 is identical to the sensor sleeve illustrated in FIGS. 1 and 2, except that the dielectric layer 12 is made of a porous and non-absorbent material. Such material may include, for example, a mesh fabric made of nylon, acrylic, polyester, or acetate, such material may also include porous polymers. Such a dielectric layer 12 allows fluid leaking from the article (e.g., a hydraulic hose) to create a conductive path through the dielectric layer and between the first electrode layer and the second electrode layer, which will change the impedance measured across the electrode layer 14, 16 from a high impedance range (e.g., mega-Ohms, kilo-Ohms, etc) to near zero Ohms. The dielectric layer 12 has conductive coating (e.g., electrode layers 14, 16) coated on both sides of the surface of the layer 12. Since the fabric is non-conductive, porous and non-absorbent, fluid leakage (conductive fluid) will be trapped in the pores and create a conductive path between the coating layers 14, 16. Therefore, the impedance (e.g., resistance) between the layers 14, 16 drops. Benefits of such sensor sleeve include detecting fluid leakage. Such sleeves are durable, sensitive, false positive resistive, low cost, easily implemented, thin and lightweight.

If the location of the leakage is desired, the conductive layer may have a small resistance. When there is a leakage at a location, the measured resistance can be correlated with the distance from the leakage point of the resistive layer to the measurement point, as illustrated in FIG. 10B (e.g., distance=(½)×Resistance/(Resistance/ft)).

Figure 11:
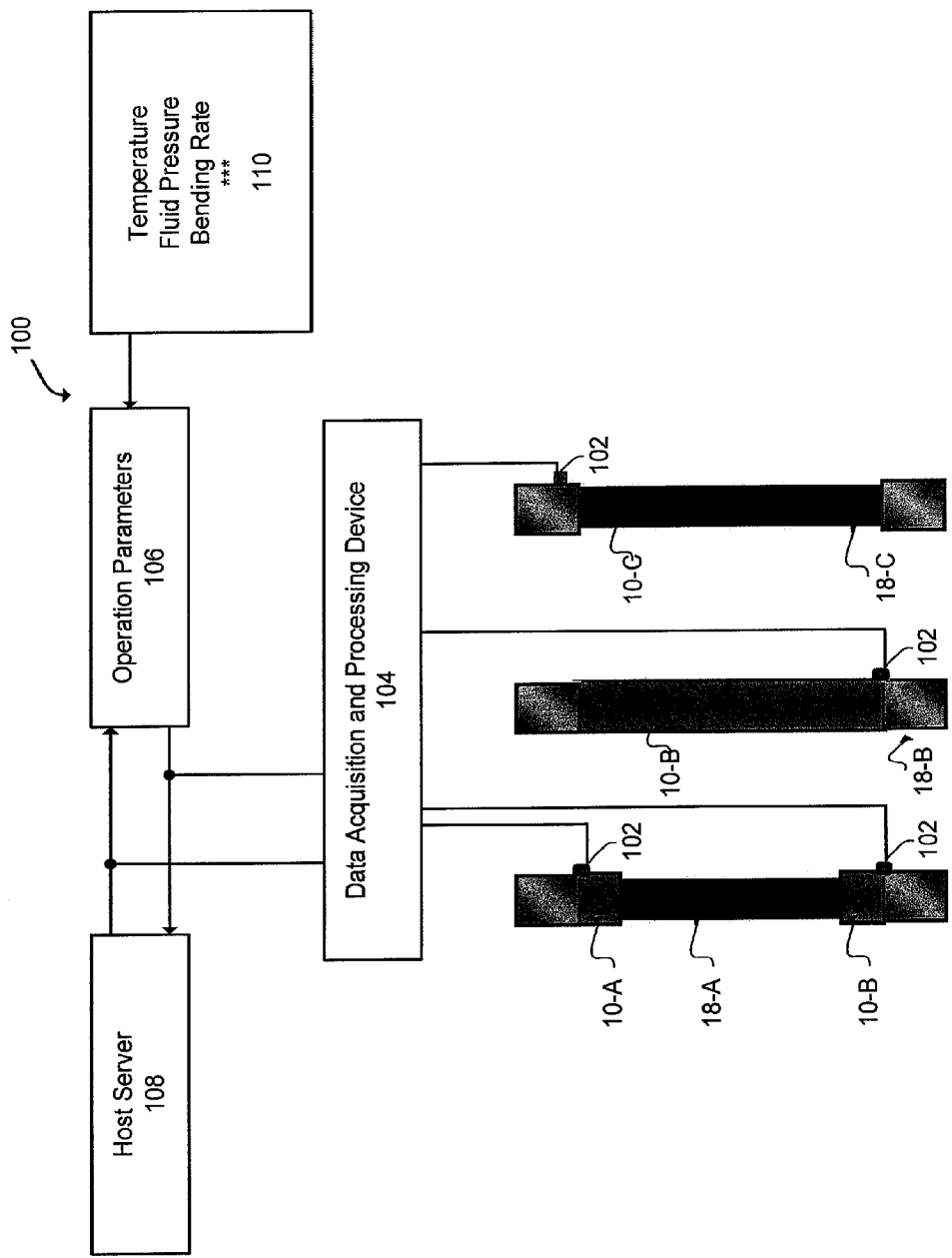
FIG. 11 is an exemplary system in accordance with aspects of the present invention.

An exemplary system 100 in accordance with aspects of the present invention is illustrated in FIG. 11. In the system 100, three embodiments of the sensor sleeve 10 are illustrated. The article 18-A includes sensor sleeves 10-A and 10-B, which cover a portion of the article 18A. In article 18-B, the sensor sleeve 10-B covers substantially the entire article 18B. In article 18-C, the sensor sleeve 10-C is an internal sensor sleeve integrally formed in at least a portion of the article 18-C, for example. The sensor sleeve 10 has one or more couplers 102 that are conductively coupled to the electrode layers 14, 16 of the sensor sleeve. The one or more couplers 102 may output their respective signals to a data acquisition device 104. In addition or alternatively, the one or more couplers may be coupled to external or internal sensor sleeves that output their respective signals to the data acquisition and processing device 104.

The information received by the data acquisition and processing device 104 may be stored in memory (not shown). The data acquisition information may also be compared to operation parameters 106 associated with the article 18 in which the sensor sleeve 10 is attached. The operation parameters 106 may be stored locally, for example by a storage device coupled to data acquisition and processing device 104 and/or received from a host server 108 coupled to the system 100. Preferably, the operation parameters 106 are stored locally. The operation parameters 106 may vary based on the type of article, environment in which the article is used, application of the article, etc. Such parameters include operating temperature, fluid pressure, bending rate, etc. and may be provided a separate storage device 110, for example.

The data acquisition and processing device 104 and host server 108 establish a wired or wireless communication link. Depending on the system configuration, preferably, data is processed locally through data acquisition and processing device 104, and only resulting information is sent to host server 108. Alternatively, data processing can be done at the host server 108, and device 104 may function solely as a data acquisition device, for example.

The host server 108 may include a database of relevant information associated with the article 18. The host server 108 may be updated and be utilized to provide information regarding the operation parameters 106, and establish reporting and aid decision making in regard to proper maintenance actions. In addition, information acquired through the data acquisition and processing device 104 may be stored at the host server 108.

Figure 12:
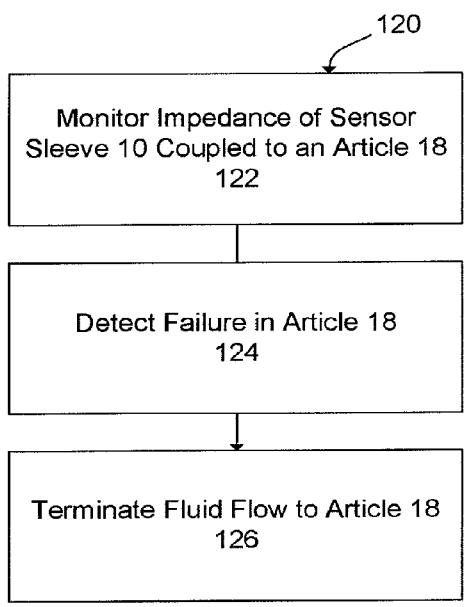
FIGS. 12 and 13 are exemplary methods in accordance with aspects of the present invention.

An exemplary method 120 for detecting failure of an article illustrated in FIG. 12. At block 122, the method includes monitoring impedance of an article 18, wherein the article includes a sensor sleeve 10 including a first electrode layer 14 covering at least a portion of a surface of the article; a dielectric layer 12 covering a least a portion of the first electrode layer 14; and a second electrode layer 16 covering at least a portion of the dielectric layer 12, wherein damage to the surface of the article covered by the first electrode layer 14, the dielectric layer 12 and the second electrode layer 16 causes the first electrode layer 14 to contact the second electrode layer 16, wherein the impedance is measured between the first electrode layer and the second electrode layer.

At block 124, the method includes detecting a failure in the article 18 based at least in part on the monitored impedance across the first electrode layer 14 and the second electrode layer 16. A failure in the article may be defined as any non-desirable performance characteristic of the article. In one embodiment, a failure is detected by comparing the impedance measured across the first electrode layer and the second electrode layer and when a prescribed difference in impedance is detected, a failure may be said to occur. A prescribed difference may be a change in impedance value of 10% or more, for example. Such a difference in impedance may occur if one or more contacts in the first electrode layer is in contact with the second electrode layer, for example.

In another embodiment, a failure is detected by comparing the impedance measured across the first electrode layer and the second electrode layer with a database of information including operation parameters associated with the article, for example the host server 108.

At block 126, upon determining a failure condition, it is desirable to terminate fluid input to the article and/or terminate operation of the machinery in which the article is attached. Therefore, upon failure of the hose, a control signal may be generated by a processor in the data acquisition and processing device 104, for example, to turn off machinery and/or flow fluid associated with the failed article. Thus, the sensor sleeve 10 may be used in a feedback loop to control one or more processes in which the article 18 is used. In addition or alternatively, it may be desired to output an audible notification and/or an electronic notification that the article has failed upon detecting the failure of the article.

Figure 13:
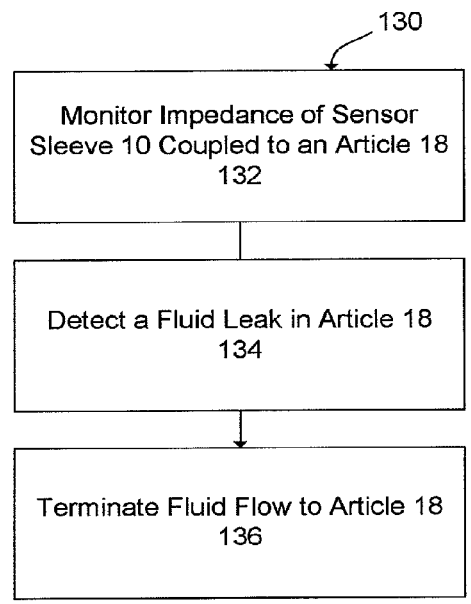

An exemplary method 130 is illustrated in FIG. 13 for detecting conductive fluid leaking in an article. At block 132, the method includes: monitoring impedance of an article 18, wherein the article includes a sensor sleeve 10 including a first electrode layer 14 covering at least a portion of a surface of the article; a dielectric layer 12 covering a least a portion of the first electrode layer, wherein the dielectric layer is porous and non-conductive; and a second electrode layer 16 covering at least a portion of the dielectric layer, wherein a leak of conductive fluid creates a conductive path through the dielectric layer 12 and between the first electrode layer and the second electrode layer, wherein the impedance is measured between the first electrode layer and the second electrode layer; and At block 134, the method includes detecting the leak of conductive fluid in the article based at least in part on the monitored impedance across the first electrode layer and the second electrode layer. In one embodiment, the leak of conductive fluid is detected by comparing the impedance measured across the first electrode layer and the second electrode layer and when a prescribed difference in impedance is detected, a failure may be said to occur. A prescribed difference may be a change in impedance value of 10% or more, for example. Such a difference in impedance may occur if one or more contacts in the first electrode layer is in contact with the second electrode layer, for example.

At block 136, upon determining a fluid leak, it is desirable to terminate fluid input to the article and/or terminate operation of the machinery in which the article is attached. Therefore, upon determination of a failure of the hose, a control signal may be generated by a processor coupled to the data acquisition device 104, for example, to turn off machinery and/or flow fluid associated with the failed article. Thus, the sensor sleeve 10 may be used in a feedback loop to control or more processes in which the article 18 is used. In addition or alternatively, it may be desired to output an audible notification and/or an electronic notification that the article has failed upon detecting the failure of the article.

In order to test the above concepts, a simple configuration of materials for the sensor sleeve was selected and tested to validate the proof of concept. A rubber sheet was chosen as the structure that the sensor skin would monitor for damage. The rubber simulates the material of a hydraulic hose and the sensor is placed near the inner layer of the hose. The sensor layer would have a protective rubber layer over it so the sensor skin is not in contact with hydraulic fluid. The sensor sleeve in this experiment includes two thin aluminum electrodes, and a dielectric medium (paper in this case to form a capacitor). Electrical alligator clamps were attached to the two aluminum electrodes and were also connected to the measurement device (a multimeter).

As expected, the initial electrical resistance of the sensor sleeve 10 was infinite, as there was no contact between the two electrodes. A probe in the form of a rod having about 1/10 inch diameter with a rounded tip that was electrically insulated by a polymer film was used as the tool to produce damage in the sensor skin.

When the load and damage was applied to the outer electrode, the electrical resistance and capacitance changed as the distance between the two electrodes narrowed. Thus, the closer the electrodes became to one another, the impedance decreased. The load was applied continuously until damage (similar to a pin hole) occurred to the outer electrode. This damage penetrated the dielectric medium and resulted in the contact of the two aluminum electrodes. This caused the electrical impedance properties (resistance and capacitance) of the skin sensor to immediately go from infinite to zero.

Figure 14:
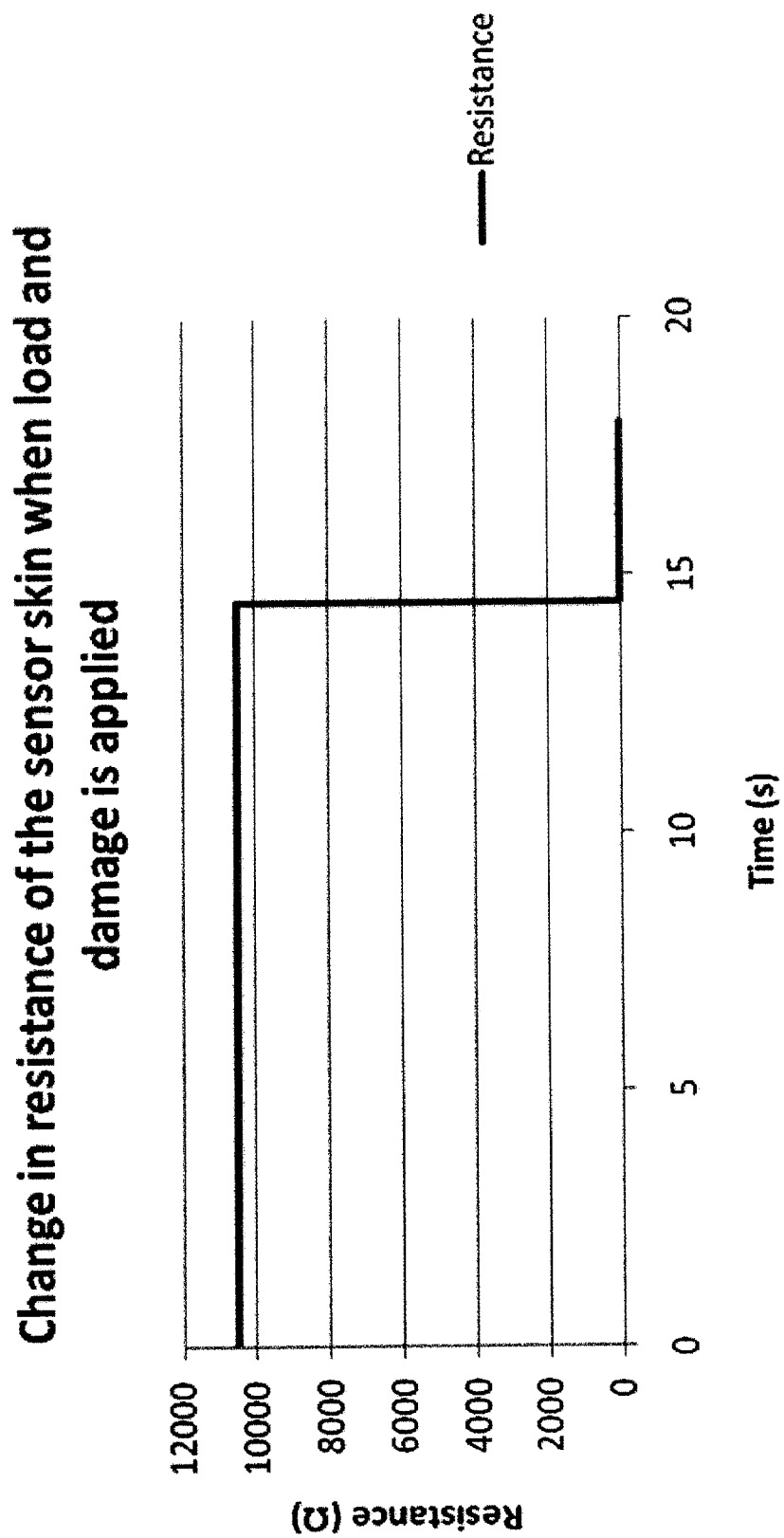
FIG. 14 is chart illustrating a change in a resistance in a sensor sleeve when in a normal condition and a failure condition.

Different trials were conducted to test the repeatability and it was observed that every time the damage penetrated through the electrodes, the resistance went from infinite to zero. A NI-Data Acquisition module NI-9219 and LabVIEW software were used to monitor the on-line data and the change in electrical resistance due to the application of load onto the surface of the outer electrode. The data obtained from LabVIEW software was then plotted using Microsoft Excel and is shown in FIG. 14. FIG. 14 clearly shows the resistance drop from infinite (e.g., 10 KOhms) to zero at about 14.5 seconds, which is when the damage occurred. A person having ordinary skill in the art will readily appreciate that reference to an impedance of infinite means that the impedance is at least an order of magnitude higher when in a open circuit state than in a short circuit state, when the impedance is said to be near zero Ohms, for example.

Note that as soon as the sensor sleeve is penetrated, the sensor sleeve reports damage. Still the damage is only to the sensor sleeve—there is no damage to the underlying rubber layer. Thus damage is detected before the structure is actually damaged and this provides time for the operator to repair or take the structure (e.g. hydraulic hose) out of service.

The concept of sensor sleeve was tested by using the electrical impedance, e.g., mainly the electrical resistance, of the sensor sleeve. Initial experiments were conducted to determine the feasibility of having an external sensor sleeve on the hose that could indicate the damage in the hose like pin holes, oil leak, etc. Aluminum was used as a conductive material and Kapton film and wax paper were used as different dielectric/insulating materials for the sensor sleeve. Two different designs were conceptualized for the hose application.

Design 1: Sensor sleeve on the outer layer of the hose.

Design 2: Sensor sleeve between the innermost rubber layer and steel layer (inside the hose).

Figure 15A:
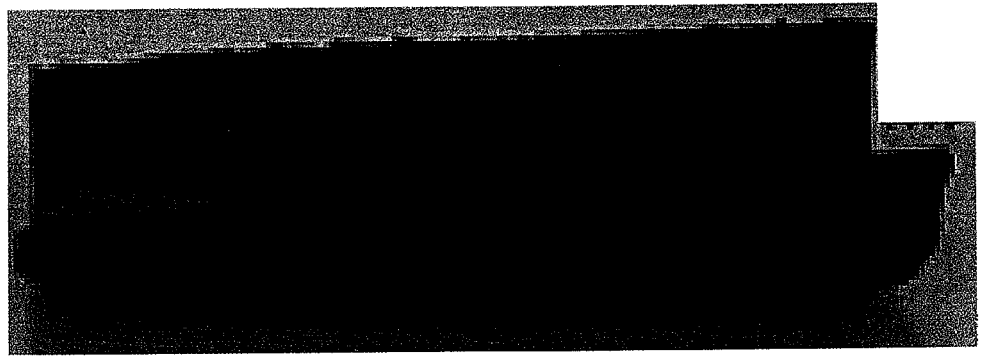
FIGS. 15A-15E illustrate development of sensor sleeve in accordance with aspects of the present invention.
Figure 15B:
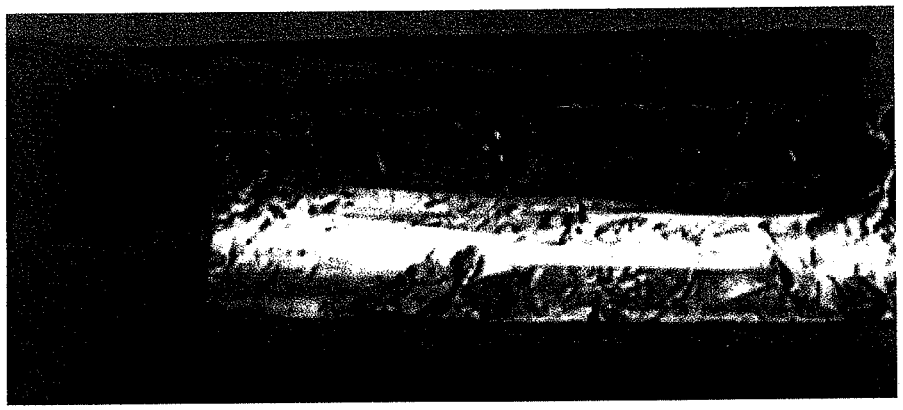
Figure 15C:
Figure 15D:
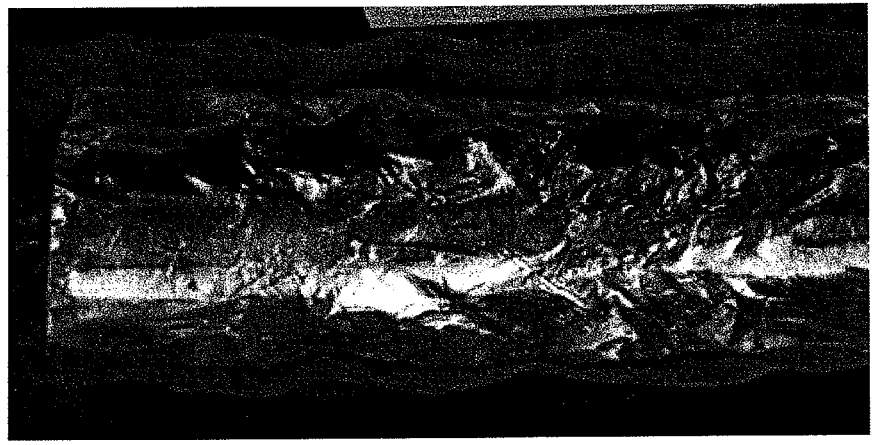
Figure 15E:
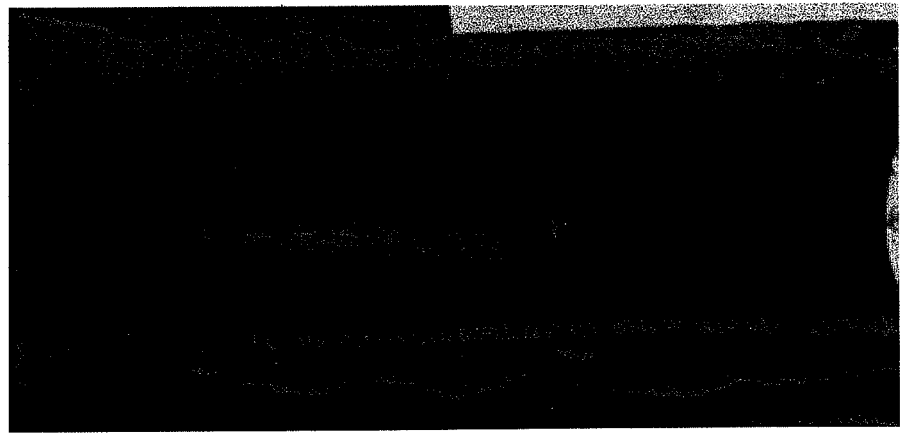

The following section describes the process involved in the development of sensor skin on the hose. For demonstration purpose, a section of hose was cut (about 15 cm in length) and a layer of sensor skin was developed on it. First, the innermost rubber layer was cut, as shown in FIG. 15A. Next, an insulating layer was glued to the innermost steel layer with an adhesive. On top of the insulating layer, a first layer of conductive aluminum was attached along the length of the hose as shown in FIG. 15B. Next, an insulating layer (wax paper or Kapton film) was put on top of the first conductive layer as shown in FIG. 15C. A second conductive layer was then added on top of the insulating layer thereby forming the sensor skin as shown in FIG. 15D. Finally, the innermost rubber layer was attached on top of the sensor skin as shown in FIG. 15E. Lead wires were attached to the conductive layers for impedance measurements.

This design utilizes the concept of developing a sensor sleeve layer on the outside of the hose. This concept can also be visualized as putting an external sensor on the hose like the sensor sleeve. The sensor sleeve can be manufactured as a separate product and can be placed on top of the outer layer of the hose. The significant advantage is the simplicity of this design as it is likely that there would be no modification to the hose itself. The sensor skin can be protected from the outside environment by covering the sensor skin with a protective rubber layer probably like the same polymer material as that of the outer layer of the hose. By this protective layer, it is possible to prevent any damage to the sensor skin from any environmental conditions and might prevent any false positive alarms from the sensor sleeve.

This design might not prevent damage happening to the hose because the sensor sleeve is going to identify the damage only after the hose has failed. But this design will prevent damage penetrating from the hose to the outside environment. The entire system can be modeled in such a way that the moment the signal from the sensor sleeve deviates from the nominal value, an alarm can be activated or the entire system can be shut down and the hose can be replaced. This design thus prevents any significant damage to the outside environment.

Figure 16A:
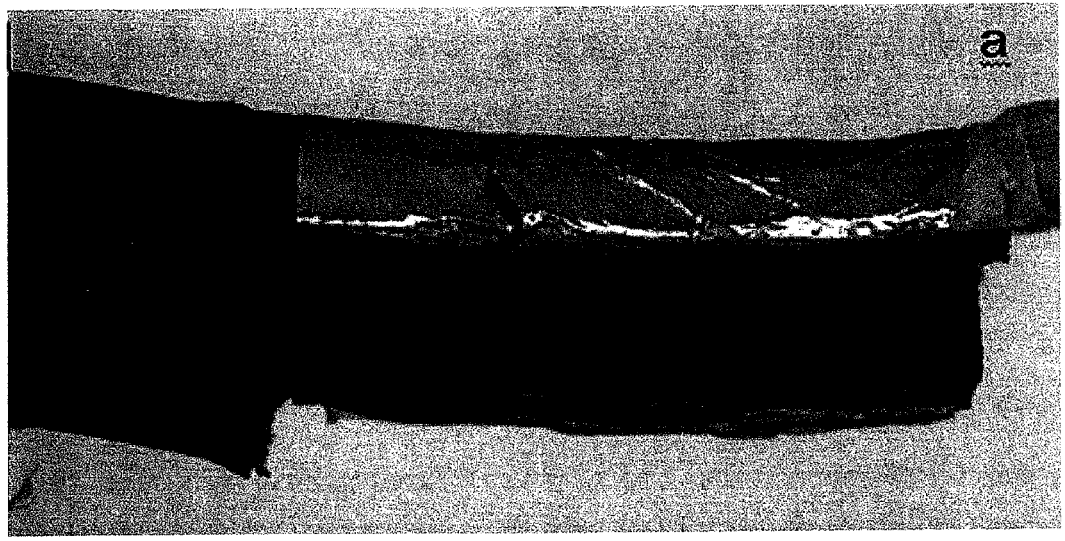
FIGS. 16A-16B illustrate a sensor sleeve on an outside surface of an article in accordance with aspects of the present invention.
Figure 16B:
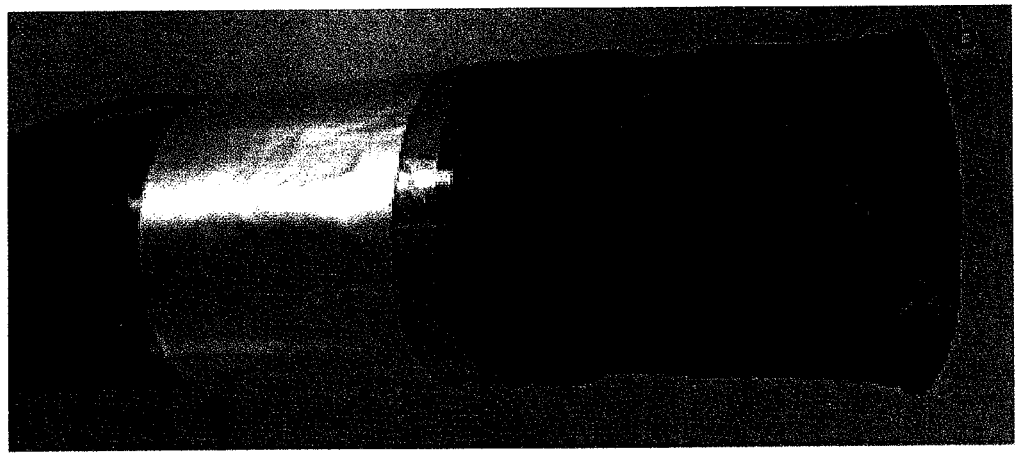

A prototype of this concept was constructed and tested. The prototype used aluminum as the conductive material and either Kapton film or wax paper as the insulating material. As described in the previous section, first layer of aluminum was attached to the outer layer of the hose followed by the insulating layer and another conductive aluminum layer on top of the insulating layer. All the layers were attached to each other using commercially available adhesive. Lead wires were taken out from the first and second conductive layers. The electrical impedance between the two layers could then be measured. Two different orientations of sensor skin were tested; sensor skin placed along the length of the hose (FIG. 16A) and the other placed circumferentially (FIG. 16B). For the second case, it can be visualized as having a sensor sleeve tape that can be attached circumferentially along the entire length of the hose.

Another design is form the sensor sleeve within the hose assembly. This design utilizes the concept of putting a layer of sensor sleeve on the inside of the hose. For example, the sensor sleeve can be built between the innermost rubber layer and first reinforcement layer. The significant advantage of this design is that it prevents damage in the hose, as any damage to the hose will have to penetrate the sensor sleeve. Such penetration will cause failure of the sensor sleeve. Thus, any damage like pin holes, oil leak, etc., beyond the innermost rubber layer can be prevented from occurring and the hose can be inspected and replaced, if necessary.

Figure 17A:
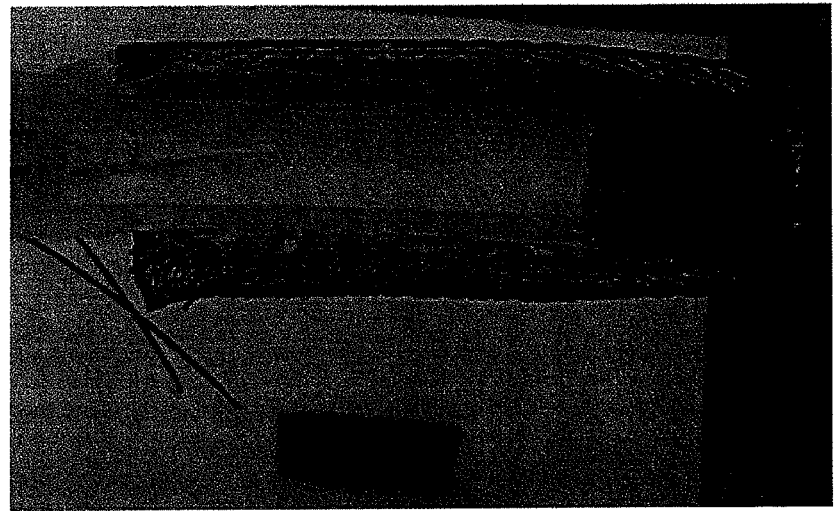
FIGS. 17A-17B illustrate a sensor sleeve on an inner surface of an article in accordance with aspects of the present invention.
Figure 17B:
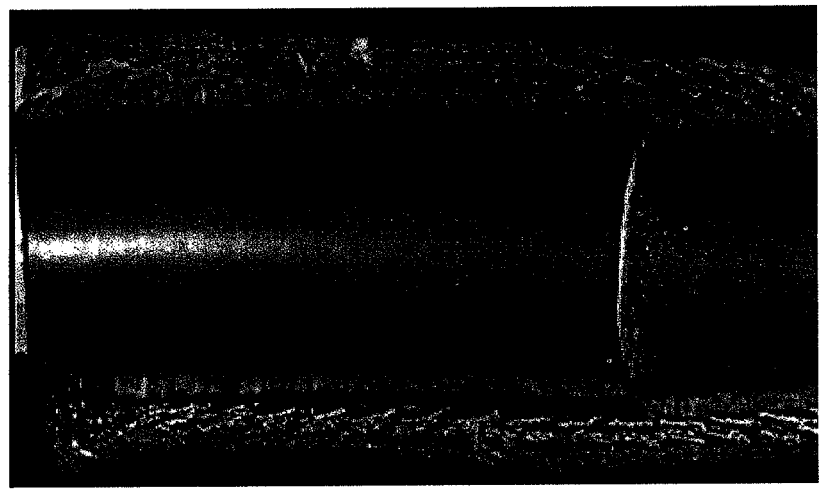

In order to prove the concept, a prototype was developed and tested. In this experiment, a portion of the inner rubber layer (about 15 cm in length) was cut thus exposing the steel reinforcement layer. Then, as described earlier, the layers of the sensor skin were attached in the proper sequence using the adhesive, as shown in FIG. 17A. The thickness of the entire sensor skin comprising of two conductive layers and insulating layer was only between 10-1000 microns. Finally, the rubber layer was glued back to its initial position as shown in FIG. 17B. Lead wires were taken out from the first and second conductive layers and the electrical impedance between the two layers was measured. The sensor sleeve was placed in the longitudinal orientation. For this experiment, there was no end fitting in the hose being tested. Hence, there was no issue of the electrode layers of the sensor sleeve coming in contact with each other due to crimping.

Test results were obtained in LabVIEW to automatically store the data from the sensor sleeve and indicate the damage occurring to the sensor skin by activating a LED signal. Two experiments were conducted; first was to simulate the pin hole damage and second was to simulate the a fluid leak (e.g., an oil leak). In the first experiment, a pin hole was simulated using a sharp pointed tool and the electrical resistance was monitored continuously. The moment the pin hole damage penetrated through the inner rubber layer and hit the sensor skin, the resistance dropped from infinite (10.5 k$\Omega$—maximum resistance capability for NI-DAQ 9219) to zero and activating the LED signal, which indicated damage to the hose. It can be observed that the damage did not penetrate the steel reinforcement layer. This further validates an advantage the sensor sleeve in predicting and preventing the damage to the hose.

Figure 18:
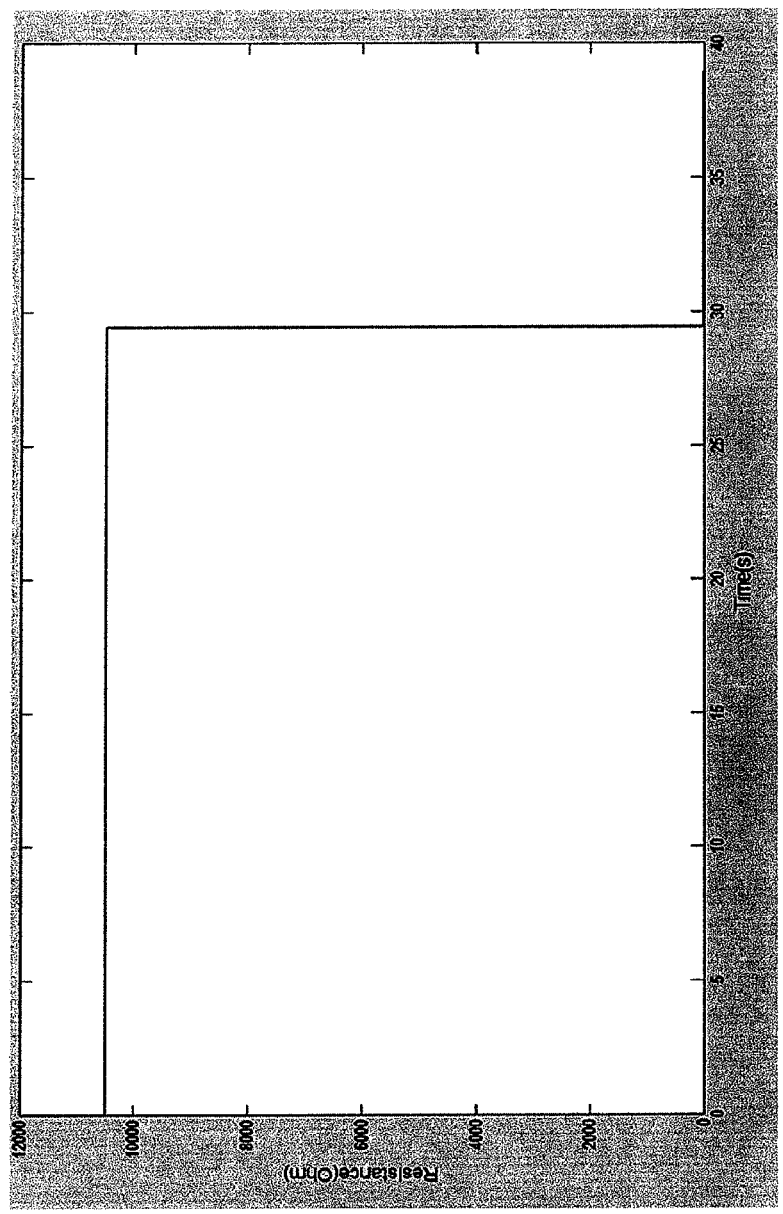
FIG. 18 is chart illustrating a change in a resistance in a sensor sleeve when in a normal condition and a failure condition.

In the second experiment, an oil leak was simulated by injecting oil using syringe into the hose until damage occurred. Approximately, 0.5 to 1 cc of oil was injected to the hose. Similar to the previous experiment, the resistance dropped from infinite to zero and activated the LED signal, indicating the damage to the hose. However, it was difficult to measure the exact amount of oil injected in the inner rubber layer. The experiments were repeated for several times and the response was repeatable. The change in resistance of the sensor sleeve is shown in FIG. 18. It can be seen that the resistance of the sensor sleeve is consistent when the hose is in the healthy condition. The sharp drop in resistance can be seen when the damage occurred to the hose. Similar result was observed for both pin hole and oil leak situations.

The sensor sleeve may also be used on a wide range of structures. For example, the sensor sleeve may be used in connection aerospace structures like aircraft, satellites, unmanned vehicles, missiles, etc. The damage to these structures from external sources like lightning, debris, and large pressure loading can be detected. The sensor sleeve's thinness makes it suitable for such applications. The sensor sleeve can be made of different materials to meet the demands of the application such as high or low temperature, abrasion, electrical conductivity, and corrosion resistance, for example.

A sensor sleeve for use on composite materials was fabricated using a Kapton film sheet between two aluminum film electrodes (0.016 mm thick), which is one way that a dry capacitor is formed. Also, wax paper was used as dielectric material and was placed between the two aluminum electrodes. Initial testing was performed to validate the proof of concept of the sensor skin using a hydraulic press. Three different spherical indenters were used in the experiment to create damage to the sensor sleeve covering the composite material. In this experiment, the sensor sleeve was placed on a loading station in the hydraulic press. The spherical indenter was attached to the top of the loading station. The load was gradually applied until the sensor sleeve was damaged. The electrical impedance of the sensor sleeve was measured using a multimeter as the load was applied. It was observed that the electrical resistance of the sensor sleeve changed from infinite to zero as the damage penetrated the dielectric medium and resulted in the contact of the two electrodes in the sensor skin. At the sensor sleeve, the composite plate showed indentation damage with the diameter of indentation measured to be 0.33".

Figure 19:
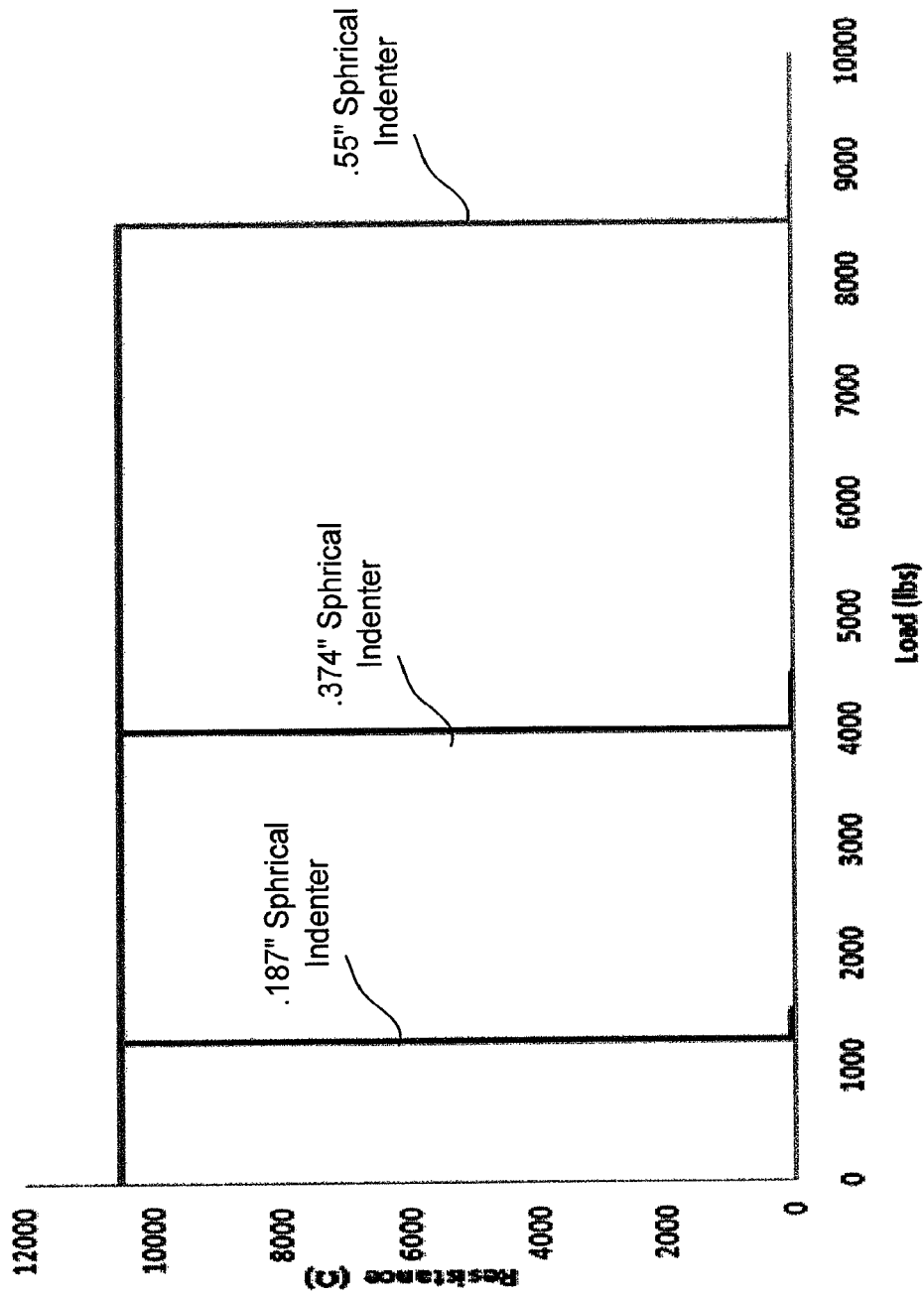
FIG. 19 is chart illustrating a change in a resistance in a sensor sleeve when in a normal condition and a failure condition for different diameter indenters.

The response of the sensor skin versus loading for three different indenter sizes is shown in FIG. 19. The graph shows change in the resistance of the sensor sleeve due to loading with the applied load shown in the x-axis and resistance of the sleeve shown on the y-axis. It can be seen from the plot that the electrical resistance of the sleeve was large in the beginning and the resistance suddenly dropped to zero as the sleeve was damaged due to loading, due to contact of the two electrodes. It is also observed that as the diameter of the spherical indenter was increased (0.187", 0.374", 0.55"), the load at which the resistance of the sensor sleeve changed from infinite to zero also increased from 1.250 klbs to 4.0 klbs, to 8.5 klbs. It can thus be concluded that the sensor sleeve is sensitive to any size of damage. For instance, the sensor sleeve will be sensitive to small damage like pin holes or large damage from impact with large particles. Having sensitivity to different size of damage is explained by considering the stress applied to the sensor sleeve. The diameter of indentation on the composite is measured and was found to be 0.128", 0.23" and 0.33" for the 0.187", 0.374" and 0.55" spherical indenters respectively. Then, the stress applied to the sleeve was calculated by knowing the area of indentation and the force applied to the sleeve. The applied stress on the sleeve due to damage was found to be around 680 MPa for all three spherical indenters. With a small diameter sphere, the area of indentation is small and the sleeve fails at a small load. With a larger diameter sphere, the area of indentation is larger and a larger load is required to cause the sleeve to fail. However, it was observed that the stress is similar for all cases. The surface of the fiberglass panel also sustained minor localized spherical shaped damage but the damage area was smaller than the area of indentation in the sensor sleeve.

From this experiment, it can be concluded that the sensor sleeve had been used as a protective layer to prevent excessive damage in the composite plate due to continuous loading as the damage in the composite plate was limited to only 0.0134" even at a very high stress level.

An experiment was also conducted to study the feasibility of the sensor sleeve to detect impact damage. A fiberglass panel was simply supported on two angle sections. A spherical indenter (steel ball) was dropped from a certain height onto the sensor skin and the variation in the resistance of the sleeve was monitored online using a data acquisition device and LabVIEW software. It was observed that the resistance of the sleeve dropped from the M-Ohms range to zero as the impact resulted in the contact of the two electrodes. This experiment shows that the sensor skin can detect dynamic loading and impact damage.

Although the principles, embodiments and operation of the present invention have been described in detail herein, this is not to be construed as being limited to the particular illustrative forms disclosed. They will thus become apparent to those skilled in the art that various modifications of the embodiments herein can be made without departing from the spirit or scope of the invention.

What is claimed is:

1. A fluid system, comprising:
   an article to be monitored for damage, the article including an outermost surface; and
   a sensor sleeve arranged over the outermost surface of the article, the sensor sleeve comprising:
      a first electrode layer covering at least a portion of the outermost surface of the article;
      a dielectric layer covering a least a portion of the first electrode layer; and
      a second electrode layer covering at least a portion of the dielectric layer,
      wherein the first electrode layer, the dielectric layer and the second electrode layer form a pressure or strain sensor operative to detect a pressure or strain on the article, and wherein damage to the article covered by the first electrode layer, the dielectric layer and the second electrode layer causes the first electrode layer to contact the second electrode layer, thereby decreasing the impedance between the first electrode layer and the second electrode layer, wherein the combination of the first electrode layer, the dielectric layer and the second electrode layer are configured to be removably attachable to the article to detect damage to the article.

2. The fluid system of claim 1, wherein one of the first electrode layer or the second electrode layer includes one or more contacts, wherein the contacts are configured to puncture through the dielectric layer and make contact with the other of the first electrode layer or the second electrode layer.

3. The fluid system of claim 2, wherein the one or more contacts are spaced apart a uniform distance along the first electrode layer or the second electrode layer.

4. The fluid system of claim 1, wherein the contacts are configured to permanently affix to the second electrode layer when a damage condition occurs.

5. The fluid system of claim 1, wherein the article is a pressurized hose having at least one hose layer operable to transfer fluids from one place to another, wherein the hose layer has a circumferential surface; and the first electrode layer covers at least a portion of the circumferential surface of the hose layer.

6. The fluid system of claim 1, wherein at least one of the first electrode layer and the second electrode layer are flexible.

7. The fluid system of claim 1, wherein the dielectric layer contains one or more voids formed between the first electrode layer and the second electrode layer.

8. The fluid system of claim 1, wherein the dielectric layer contains an auxetic material- and a non-conductive material, wherein the auxetic material is spaced along the dielectric layer.

9. The fluid system of claim 1, wherein the dielectric layer is layer of fabric.

10. The fluid system of claim 1, wherein the dielectric layer includes a wire embedded in the dielectric layer.

11. The fluid system of claim 1, wherein the first electrode layer, the second electrode layer and the dielectric layer have a combined mechanical impedance that matches mechanical impedance of the article.

12. The fluid system of claim 1, further comprising a coupler having a first end coupled to first electrode layer and a second end coupled to the second electrode layer.

13. The fluid system of claim 12, wherein the coupler is configured to couple an associated measuring device to the sensor sleeve, wherein the associated measuring device is configured to measure impedance and/or capacitance across the first electrode layer and the second electrode layer.

14. The fluid system of claim 1 further comprising a protective layer that protects at least the second electrode layer from an environment in which the article is used.

15. The fluid system according to claim 1, wherein the article comprises reinforcement layers.

16. The fluid system according to claim 15, wherein the reinforcement layers comprise steel reinforcement layers.

17. A method for detecting failure in an article of a fluid system, the article including an outermost surface having a sensor sleeve arranged over the outermost surface of the article, the method comprising:

removably attaching the sensor sleeve to the article;

monitoring impedance of the sensor sleeve, wherein the sensor sleeve comprises a first electrode layer covering at least a portion of outermost surface of the article; a dielectric layer covering a least a portion of the first electrode layer, and a second electrode layer covering at least a portion of the dielectric layer, wherein the first electrode layer, the dielectric layer and the second electrode layer form a pressure or strain sensor operative to detect a pressure or strain on the article, and wherein damage to the article covered by the first electrode layer, the dielectric layer and the second electrode layer causes the first electrode layer to contact the second electrode layer, wherein the impedance is measured between the first electrode layer and the second electrode layer; and detecting a failure in the article based at least in part on the monitored impedance across the first electrode layer and the second electrode layer.

18. The method of claim 17, wherein the step of detecting includes determining if one or more contacts in the first electrode layer is in contact with the second electrode layer.

19. The fluid system of claim 1, wherein the article comprises an inner tube that contacts a fluid flowing through the article, at least one reinforcement layer arranged over the inner tube, and an outer cover arranged over the reinforcement layer, wherein an outer surface of the outer covering forms the outermost surface of the article.

20. The fluid system of claim 2, wherein the one or more contacts are spaced apart a non-uniform distance along one of the first electrode layer or the second electrode layer.

* * * * *